United States Patent [19]

Okrongly

[11] Patent Number: 4,933,410

[45] Date of Patent: Jun. 12, 1990

[54] COVALENT ATTACHMENT OF MACROMOLECULES ON SUBSTRATE SURFACES

[75] Inventor: David Okrongly, Sunnyvale, Calif.

[73] Assignee: Applied Immunesciences, Inc., Menlo Park, Calif.

[21] Appl. No.: 330,207

[22] Filed: Mar. 29, 1989

[51] Int. Cl.$^5$ .............................................. C08F 8/30
[52] U.S. Cl. .................................. 525/333.6; 525/374
[58] Field of Search .............................. 525/333.6, 374

[56] References Cited

U.S. PATENT DOCUMENTS

| | | | |
|---|---|---|---|
| 3,875,114 | 4/1975 | Swiger | 525/333.6 |
| 3,956,219 | 5/1976 | Smithwick, Jr. . | |
| 3,974,110 | 8/1976 | Patchornik et al. . | |
| 3,995,094 | 9/1976 | Crosby et al. . | |
| 4,081,329 | 3/1978 | Jaworek et al. . | |
| 4,226,958 | 10/1980 | Smith et al. . | |
| 4,419,444 | 12/1983 | Quash . | |
| 4,654,299 | 3/1987 | Lentfer . | |
| 4,657,873 | 4/1987 | Gadow et al. . | |
| 4,736,019 | 4/1988 | Bellattar et al. . | |

FOREIGN PATENT DOCUMENTS

| | | |
|---|---|---|
| 0107119 | 5/1984 | European Pat. Off. . |
| 0294059 | 7/1988 | European Pat. Off. . |

*Primary Examiner*—Bernard Lipman
*Attorney, Agent, or Firm*—Bertram I. Rowland

[57] ABSTRACT

Uncrosslinked polystyrene surfaces are derivatized under Friedel-Crafts conditions in a tetramethylenesulfone solvent using a substituted N-hydroymethyl acetamide derivatizing agent. The substitutent is subject to nucleophilic substitution to allow for the binding of a wide variety of molecules, particularly specific binding pair members, to the surface. Clarity is maintained for monitoring observation of events on the surface through the polystyrene.

12 Claims, No Drawings

COVALENT ATTACHMENT OF MACROMOLECULES ON SUBSTRATE SURFACES

INTRODUCTION

1. Technical Field

The subject field concerns functionalizing polystyrene surfaces, particularly labware, for covalent conjugation of molecules.

2. Background

With the increasing expansion of biological research and commercial biological applications, there has been a concomitant increasing need for laboratory equipment capable of specifically binding to complementary ligands and receptors. In order to provide solid substrates, particularly labware, for specific complex formation, it is necessary to bind a wide variety of ligands and receptors, frequently proteins, to the surface. The binding should provide a surface which minimizes non-specific binding, minimizes loss of the surface bound molecules during the processing, and provides for a high density of the compound bound to the surface in a manner which allows for efficient complex formation.

At the present time, there is no simple and reliable method for covalently attaching a macromolecule to the surface of polystyrene labware, particularly when clarity retention is desired, as well as a high density of the attaching macromolecule. Almost all common organic solvents, used to chemically activate or derivatize crosslinked polystyrene for solid phase peptide synthesis, particularly solvents such as methylene chloride and DMF, readily dissolve or badly haze uncrosslinked polystyrene. Many of the known solid substrate bound macromolecules exhibit a low surface concentration of the macromolecule, or exhibit only partial biological activity of the bound macromolecule. In some cases, the overall charge of the macromolecule is changed, as is the case in protein conjugation techniques employing active esters (which transform an amino group on the protein to an amide). In other cases, the yield of macromolecules bound to the surface of the substrate is low. In still other cases, surface activation of the substrate adds color to the substrate, thus eliminating or reducing the effectiveness of the substrate in assays such as enzyme linked immunosorbent assays (ELISA).

A continuing interest exists, therefore, in the development of improved activated solid substrates, in improved activated solid substrates bound with covalently attached macromolecules, and in the improved processes for producing these compositions.

Relevant Literature

Activated substrates, including polystyrene, and various biologically active substances bound to the substrate, are described in U.S. Pat. Nos. 4,736,019; 4,657,873; 4,654,299; 4,419,444; and 4,081,329. Functionalization of polystyrene is also described in U.S. Pat. Nos. 3,956,219; 3,886,486; 3,974,110; 3,995,094; and 4,226,958. See also, copending application Ser. Nos. 055,528 and 051,917, filed May 29, 1987 and May 19, 1987, respectively, and EPO Application Serial No. 88/304516.3. The use of N-hydroxymethyl 2-chloroacetamide in nitrobenzene/$H_2SO_4$ to derivatize polymers containing polystyrene is described in EPO Application Serial No. 83/109905.6.

SUMMARY OF THE INVENTION

Formed substantially uncrosslinked polystyrene products are functionalized employing hydroxymethylamides for electrophilic substitution on the phenyl groups. The substituted-methylamides include a substitutable functionality permitting nucleophilic substitution, while being stable under the conditions of aryl substitution. The resulting functionalized polystyrene may be used for reacting with a wide variety of functionalities, particularly associated with macromolecules, to provide for a high density of covalently bonded macromolecules. The method employs a polystyrene insoluble solvent as the solvent for the aromatic electrophilic substitution. The resulting functionalized polystyrene may be reacted with macromolecules to provide for surfaces useful for complex formation between complementary binding pairs.

DESCRIPTION OF THE SPECIFIC EMBODIMENTS

In accordance with the subject invention, polystyrene surfaces are functionalized by reaction with hydroxymethylamides or derivatives thereof in a polystyrene insoluble solvent, particularly tetramethylenesulfone (TMS), under aromatic electrophilic substitution conditions. The amides are characterized by having a functionality capable of nucleophilic substitution under mild conditions, while stable under the conditions of aromatic electrophilic substitution. The resulting functionalized polystyrene may be reacted with various functionalities capable of nucleophilic substitution, particularly macromolecules, to provide for a surface which may be used for complex formation between specific binding pairs. Of particular interest is the functionalization of labware which can be used in the isolation of a wide variety of substances which binds specifically to a complementary pair member, in assays, as affinity columns, and the like.

The polystyrene objects which are activated, will be for the most part non-crosslinked, usually having fewer than about 0.5% crosslinks, more usually fewer than about 0.1% crosslinks. The polystyrene products are normally molded, so as to provide for a smooth surface with few indentations or canyons, so that molecules may be bound to the surface and be readily available for binding to other molecules.

The solid substrate may exist in any form, including, but not limited to: reaction vessels, reagent tubes, beakers, cuvettes, columns, microtiter plates, Petri dishes, fabricated articles, beads, rods, fibers, strands, membranes, discs, or plates. The articles are normally formed by molding polystyrene at least substantially free of crosslink, usually resulting in a clear, smooth surface.

Because of the clarity of the substrate, one can see through the walls of the labware and can have efficient transmission of light, as needed. This clarity is particularly important in assays, where colorimetry or fluorimetry is involved, and light is observed as transmitted through a wall. The other factor is the smoothness of the surface, which avoids having large canyons or crevices in relation to molecular dimensions. Where the product has an uneven surface, molecules which are bond to the surface may bind within the crevice or along the walls of the crevice, making the molecule unavailable for binding to a complementary specific binding member. Therefore, even where one can obtain a high degree of activation of the surface, so that a large number of molecules may be covalently bonded to the surface, only a portion of the molecules will be available for binding to their complementary member. By contrast, with polystyrene molded surfaces, the surface is fairly uniform and flat so that molecules that are covalently bonded to the surface extend upwards from the surface, usually allowing easy access to sites on the molecule for binding to complementary pair members. Thus, receptors such as surface membrane proteins and antibodies may be bound to the surface, where their binding sites are readily available for binding to complementary ligands.

Retention of the desirable properties of the molded polystyrene is achieved using functionalized Y-methyl acetamides, where the Y-methyl group reacts with the polystyrene in a TMS solvent in the presence of a Lewis acid catalyst under mild conditions, and Y is a moiety capable of undergoing nucleophilic substitution by an aryl group, e.g. benzene in the presence of a Lewis acid catalyst. The α-acyl functional group of the Y-methyl amide is a group which is stable under the aromatic electrophilic substitution conditions, but can be readily displaced by a Lewis base under nucleophilic substitution conditions.

The compounds used for functionalizing the polystyrene will for the most part have the following formula

X(R)CHCONHCH$_2$Y wherein:

R is an alkyl group of from 1 to 3, more usually from 1 to 2 carbon atoms or hydrogen, usually hydrogen;

X is a halogen (including pseudohalogen), where the halogen is of atomic number of at least 17, wherein X may be chlorine, bromine, or iodine, and the pseudohalogens, such as arylsulfonate esters, sulfonium salts, or the like. Usually, when other than halogen, the substituent on the α-carbon atom of the acyl group will be of at least about 2 carbon atoms and not more than about 10 carbon atoms, usually not more than about 8 carbon atoms, and may have from 1 to 6, more usually from 1 to 5, and preferably from 1 to 4 heteroatoms, which include halogen and chalcogen (oxygen and sulfur), where any counterion is not included in the limitations. While many other functional groups may be present, such as cyano and nitro, for the most part they do not play a useful role and the compounds are not generally available.

Y may be the same or different from X, usually different, and is a group capable of nucleophilic substitution, particularly oxy-derivatives, halides and pseudohalides, where the oxy-derivatives may be esters, either organic or inorganic, or ethers. Y will usually be of not more than 20 carbon atoms, usually not more than 12 carbon atoms and up to about 8, usually not more than about 6 heteroatoms, Y groups include hydroxy halogen of atomic number of at least 17, pseudohalides such as arylsulfonate esters, esters such as phosphates, carboxylates, imidates, etc, ethers, such as alkyl, aryl, oxyalkyl, etc.

N-hydroxymethyl acetamides which find use are the 2-substituted N-hydroxymethyl acetamides, including but not limited to N-(hydroxymethyl)-2-chloroacetamide, N-(hydroxymethyl)-2-bromoacetamide, N-(hydroxymethyl)-2-iodoacetamide, N-(hydroxymethyl)-O-(p-bromobenzenesulfonyl)glycolamide, N-(hydroxymethyl)-O-(p-toluenesulfonyl)glycolamide, N-(hydroxymethyl)-2-acetamidopentamethylenesulfonium iodide, and N-(hydroxymethyl)(2-acetamido)pentamethylenesulfonium trifluoroacetate. The synthetic reaction for each of these individual compounds is shown in the Examples.

The N-hydroxy compounds may be derivatized or prepared directly with the particular acid or hydroxyl replacing group in the reaction mixture during the N-substitution of the α-substituted acetamide or using a formaldehyde derivative such as α-chloromethyl methoxyethyl ether.

The activation of the polystyrene will occur under mild conditions in a solvent which neither dissolves nor swells the polystyrene. While the preferred solvent is TMS, other solvents which are less efficient may find use, such as acetonitrile, nitromethane, and DMSO (dimethyl sulfoxide).

The reaction will be carried out in the presence of a strong acid, particularly a protonic acid, preferably an organic acid, such as trifluoroacetic acid, trifluoromethanesulfonic acid, methanesulfonic acid, sulfuric acid, phosphoric acid, hydrogen fluoride. The concentration of the acid will generally range from about 0.1 to 2 M. The reaction will normally be carried out in the substantial absence of atmospheric moisture, which can be achieved by covering the reaction mixture, providing for an inert atmosphere, or the like.

The polystyrene surface is contacted with the N-(Y-methyl) acetamide compound within a temperature and time range suitable for activating the surface of the substrate. Generally, the temperature will range from about −5° C. to about 60° C., preferably about 0° to about 30° C., and the activation time is from about 5 min to about 48 h, usually from about 2 to about 8 h. The concentration of the N-(Y-methyl) acetamide compound is typically between about 0.01 to 2 M, usually between about 0.05 to 0.5 M. For most applications, the use of at least about 0.05, usually 0.1 ml of reaction solution per square centimeter of solid substrate surface area is sufficient to provide for the desired level of activation by reaction of electrophilic groups onto the surface of the substrate.

Before the conjugation of the macromolecule, the surface of the substrate may be freed of any unreacted N-(Y-methyl) acetamide compound by washing with a buffer and/or water. The particular material employed for the washing step is not critical to the invention, and is chosen for convenience, so long as the conditions do not affect the substitutable group of the amide. Substitution of the substitutable group may be conducted immediately after activation, or at some interval of time, since the surface is stable when stored in an inert environment.

The activated polystyrene surface may now be reacted with compounds capable of substituting the substitutable groups. These compounds for the most part will have atoms having unshared pairs of electrons, such as nitrogen, oxygen and sulfur. For the most part, these compounds will be peptides, particularly proteins. Where peptides are reacted, the reaction will be under mild conditions by contacting solutions of the molecules at concentrations ranging from about $10^{-6}$ to 2 g/ml, more usually from about $10^{-3}$ to 1 g/ml, at a pH in the range of about 6 to 10, more usually about 7 to 9.5.

The medium will normally be buffered with a convenient buffer, e.g. phosphate, borate, or other inorganic or organic buffer, which cannot compete for reaction with the substitutable group on the surface. The concentration of the buffer will generally be from about 0.01 to 0.5 M. Also included in the medium may be various salts, particularly alkali metal halide salts, where the concentration of the salt will generally range from about 0.01 to 0.5 M.

The temperature will generally range from about 0° to 40° C., more usually from about 10° to 30° C. The time for the reaction will vary depending upon the substitutable group, the nature of the substituting group, the other components in the reaction medium, and the like. Generally, the incubation time will be at least about 5 min, usually at least about 30 min, and not more than about 24 h, usually not more than about 12 h.

The resulting activated polystyrene surface may be analyzed by electron spectroscopy for chemical analysis (ESCA) to determine the percent amount of elements on the surface of the substrate. Table 1 in Example 4 illustrates the data obtained for a polystyrene tissue culture flask (25 cm$^2$).

Groups which may be substituted onto the polystyrene surface include, but are not limited to proteins, particularly biologically active proteins; ligands, such as haptens, and antigens; receptors, such as antibodies, monoclonal antibodies and antibody fragments, enzymes, and naturally occurring receptors, such as surface membrane proteins, lectins, and blood proteins (e.g., thyroxine binding globulin); complexing agents, such as cryptands, crown ethers, porphyrins, and phthalocyanines; nucleic acids, such as RNA, DNA, oligonucleotides unnatural nucleotides, e.g. methylphosphonates; peptides; indicator substances, such as dyes, fluorescers, and chemiluminescers; antibody binding proteins (such as Staphylococcal protein A or complement component enzymes); ligands such as cerebrosides, sphingomyelin and gangliosides; glycosides; enzymes, where the enzymes are used as catalysts rather than receptors, enzyme substrates, inhibitors, or co-factors; or other molecules which may be of interest for the detection of the same or different molecules; or used for the manipulation, isolation, reaction, interaction, or other phenomena, where a result of interest is produced.

After completion of the reaction, the reaction mixture may be discarded and the surface washed with a solvent, buffer, or water to remove any residual non-covalently bound materials. The particular wash solution employed for this washing step is not critical to the invention, and is chosen for convenience.

The uses of the product of the present invention—the polyaryl addition polymer either in its activated state, or containing a covalently attached macromolecule or other molecule—are many and varied, as follows.

The modified devices find a wide variety of uses in diagnosis and in therapy, particularly ex vivo, in the isolation of cells from blood, other physiological fluids, or dispersed tissue. Because of the high density of various compositions which may be bound to the surface, where complementary binding members may be found on cells, the cells may be bound to the surface, thus separating subsets of cells from a mixture of cells. In addition, this method of separation allows for high levels of viability of the cells and ease of cell recovery. Because the clarity of the surface is maintained, the binding of cells to the surface may be monitored, as well as the processing of the cells, such as expansion with mitotic agents and lymphokines, activation with immune complexes, or the like.

The subject surfaces may also be used in diagnostic assays to provide for efficient binding of specific binding pair members to the surface. Because of the clarity of the surface, light can be transmitted through the sample and the bottom of the container, e.g., a microtiter well plate. Furthermore, because of the high efficiency of binding, particularly where the possibility of binding at multiple sites exists, washing can be relatively thorough and vigorous, to ensure the substantial absence of any non-specifically bound components of the assay.

The following Examples are offered by way of illustration and not by way of limitation.

EXPERIMENTAL

Example 1

Several N-hydroxymethyl acetamide compounds were prepared by suspending a 2-haloacetamide compound (25 g, 267 mmol in water (75 ml) and 37% formaldehyde (8.01 g, 20 ml, 267 mmol), and treating the suspension with $K_2CO_3$ (25 g, 18 mmol). A solution forms after stirring for several min. The reaction mixture is then placed at 4° C. overnight, filtered, and dried in vacuo (0.01 mm, 18 h, at room temperature).

Using the above process with 2-chloroacetamide yielded 12.5 g (38%) of N-(hydroxymethyl-2-chloroacetamide (Compound 1), as colorless crytals: melting point, 98°–99° C.

Using the above process with 2-bromoacetamide yielded 47% of N-(hydroxymethyl)-2-bromoacetamide (2), as colorless crystals: melting point, 88°–89° C.

Using the above process with 2-iodoacetamide yielded 43% of N-(hydroxymethyl)-2-iodoacetamide (3), as colorless crystals: melting point, 117° 118° C.

Example 2

N-(hydroxymethyl)-O-(p-bromobenzenesulfonyl) glycolamide (4) was prepared by treating a solution of O-(p-bromobenzenesulfonyl)glycolamide (7.1 g, 24 mmol) in DMF (21 ml) with 37% formaldehyde (2.2 g, 5.4 ml, 72 mmol) and $K_2CO_3$ (1 ml of a 50 mg/ml water solution, 0.36 mmol). After 30 min, the reaction was diluted with 10 times the volume water, cooled on ice, and filtered. The solid was dried in vacuo and recrystallized from EtOAc to give 5.9 g (76%) 4 as colorless crystals: melting point, 99°–100° C.

N-(hydroxymethyl)-O-(p-toluenesulfonyl) glycolamide (5) was prepared using the same procedure as for 4, resulting in a 70% yield of 5 as colorless crystals: melting point, 91°–93° C.

N-hydroxymethyl)-2-acetamidopentamethylenesulfonium iodide (6)

(6) was prepared by chilling a solution of 3 (1.0 g, 4.6 mmol) and pentamethylene sulfide (2.4 g, 2.5 ml, 24 mmol) in acetone at 4° C. for 48 h. The solid that crystallizes is collected on a glass frit, washed with ether, and dried in vacuo to yield 560 mg (38%) of the iodide salt of 6, as colorless crystals: melting point 93°–95° C.

N-(hydroxymethyl)-2-acetamidopentamethylenesulfonium trifluoroacetate (6)

(6) was prepared by eluting the iodide salt prepared above through a 10-fold excess AG1-X4 ($-O_2CCF_3$) column with water. The UV active (254 nm) fractions were lyophilized, dried in a rotovap three times from anhydrous acetonitrile, and dried in vacuo (0.05 mm, 18 h, room temperature) to give a quantitative yield of 6

(based on the starting iodide), as light yellow crystals: melting point 65.5°–67° C.

Example 3

Preparation of a substrate surface

A 0.2 M solution of N-hydroxymethyl acetamide derivatives 1-6 in tetramethylenesulfone (TMS), was combined in a 1:1 ratio with a 2 M trifluoromethylsulfonic acid (TFMSA) solution in TMS, and the reaction solution was immediately added to the polystyrene surface to be derivatized. Tissue culture flasks (commercially available from Corning) were capped tightly with the screw-top caps provided by the manufacturer. Microtiter plates (96-, 24-, or 6-well, non-irradiated polystyrene) or Removeawells (Immulon 1; commercially available from Dynatech) were covered with adhesive-backed Mylar tape. The reaction solution was left in contact with the polystyrene surface for 5 h at room temperature, washed with water until odorless, and air-dried at room temperature overnight. The surfaces were stable for at least two weeks in a dry, light-free environment.

Example 4

Solutions of each of the N-hydroxymethyl acetamide compounds 1-6 were made at a concentration of 0.1 M with 1 M TFMSA in TMS, and the resulting solutions were used to activate both tissue culture flasks (commercially available from Corning) and microtiter plates (Immulon I, available from Dynatech), by contacting the solution with the flasks or plates for 5 h at room temperature. Only non-irradiated polystyrene was used for the activation step. For both tissue culture flasks and microtiter plates, at least 0.1 ml of reaction solution per square centimeter of polystyrene surface area was used. The reaction mixture was protected from moisture in the air by tightly capping the tissue culture flask, or covering the microtiter plate with Mylar adhesive tape, immediately after the introduction of the reaction solution. The surfaces prepared, surfaces 7-12, are outlined below:

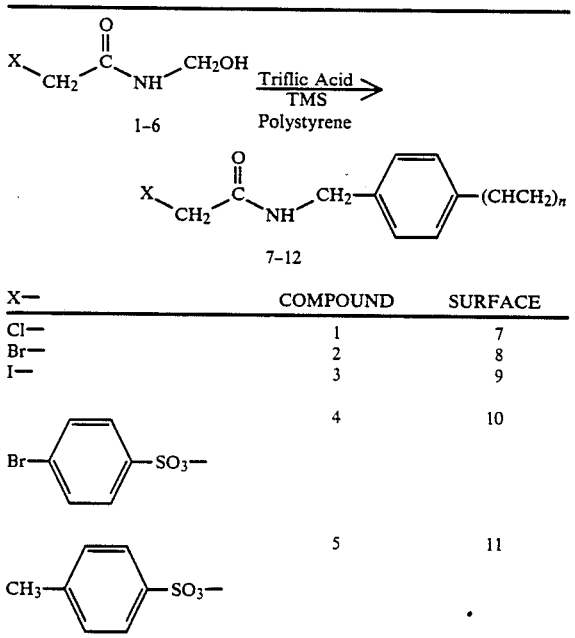

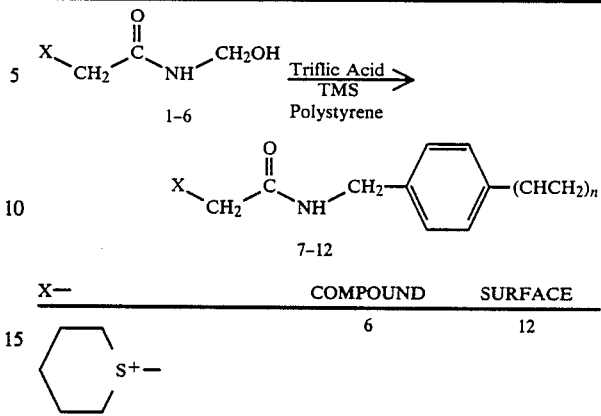

| X— | COMPOUND | SURFACE |
|---|---|---|
| 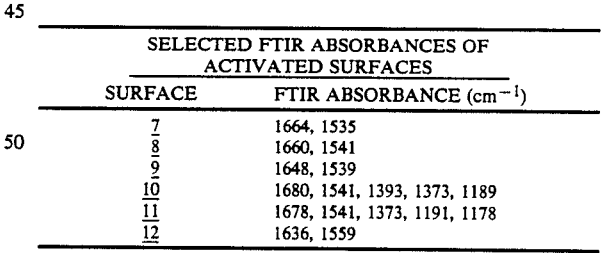 | 6 | 12 |

ESCA data for T-25 (25 cm²) tissue culture flasks having surfaces 7-12 is shown in the following Table:

| SURFACE | ELEMENT % | | | | | | | |
|---|---|---|---|---|---|---|---|---|
| | C | N | O | F | Cl | Br | I | S |
| 7 | 81.8 | 5.9 | 6.9 | * | 5.4 | * | * | * |
| 8 | 83.0 | 5.4 | 5.9 | * | * | 5.2 | * | * |
| 9 | 78.1 | 7.8 | 7.0 | * | * | * | 7.1 | * |
| 10 | 73.0 | 4.5 | 14.0 | 1.1 | * | 3.3 | * | 4.5 |
| 11 | 78.0 | 4.0 | 14.0 | * | * | * | * | 4.0 |
| 12 | 82.0 | 3.6 | 8.4 | 2.3 | 0.2 | * | * | 3.1 |

The starting polystyrene was found to have 3-5% oxygen on its surface.

Example 5

Attenuated Total Reflectance Fourier Transform Infrared Spectroscopy (ATR-FTIR) was also applied to analyze the derivatized polystyrene surfaces 7-12. In all cases, a strong amide I and amide II absorbance were detected. A series of strong symmetric and asymmetric O-S-O absorbances was also detected for the sulfonate esters 10 and 11. The data are summarized in the table next page.

| SELECTED FTIR ABSORBANCES OF ACTIVATED SURFACES | |
|---|---|
| SURFACE | FTIR ABSORBANCE (cm⁻¹) |
| 7 | 1664, 1535 |
| 8 | 1660, 1541 |
| 9 | 1648, 1539 |
| 10 | 1680, 1541, 1393, 1373, 1189 |
| 11 | 1678, 1541, 1373, 1191, 1178 |
| 12 | 1636, 1559 |

Example 6

Protein binding protocol with $^{35}$S-labeled human IgG.

Removeawell strips having surfaces 7-11, as produced in the previous example, and Immulon 1 were coated with $^{35}$S labeled human IgG (spec. act. >3 dpm/ng) in PBS at 20 µg/ml, 100 µl/well for 16 h at room temperature. Surface 12 was treated in the same fashion, except the coating buffer was 0.1 M borate, pH 9.2. After incubation, the radioactive solution was carefully removed, and the wells were rinsed 10 times with PBS. The wells were broken apart, placed in 1% SDS (3 wells/10 ml) and incubated at 55° C. for 14 h. The wells were removed from the SDS, given one more PBS rinse, and counted in Fisher Scintiverse II. The wells were recounted 24 h later. Agreement between the two counts was always within 5%.

The results are tabulated below, and show that the derivatized polystyrene surfaces bound 2.2 to 2.8 times as much protein as the underivatized Immulon I.

| SURFACE | IgG SURFACE DENSITY (ng/cm$^2$) |
| --- | --- |
| Immulon 1 ™ | 100 |
| 7 | 225 |
| 8 | 260 |
| 9 | 250 |
| 10 | 281 |
| 11 | 248 |
| 12 | 240 |

Example 7

A macromolecule-bonded, activated substrate, produced according to the present invention, was used in an ELISA protocol.

Serial dilutions of a 1 mg/ml solution of rabbit ×human IgG (commercially available from Jackson Immunoresearch) were used to provide concentrations of 100, 70, 30, 10, 3, and $1 \times 10^{-4}$ mg/ml solutions in 0.1 M borate, pH 9.2. Four polystyrene wells (activated with Compound 7 according to the present invention) with 100 μl of each concentration were coated with the antibody for 16 h in a covered microtiter plate at room temperature (no rocking). Four more wells were coated with buffer alone. The antibody solution was shaken out and tapped dry on a piece of toweling. The non-specific binding sites in all wells were blocked with 200 μl of 5% BSA in PBS, incubated in a covered plate for 16 h at room temperature. The plate was washed five times with PBS/0.02% Tween 20 (using a Wheaton gun), and all wells were incubated 3 h at room temperature with 100 μl of a $30 \times 10^{-4}$ mg/ml human IgG solution (in PBS, and available from Sigma). The plate washed 5 times with PBS/0.02% Tween 20, and 100 μl of a 1:3000 dilution goat×human IgG(H+L)—AP (alkaline phosphatase) conjugate (commercially available from Jackson Immunoresearch), in PBS/0.02% Tween 20, was added to all wells for 3 h at room temperature in a covered plate. The plate was washed 3 times with PBS/0.02% Tween 20, and 3 times with PBS. To all wells was added 100 μl of alkaline phosphatase substrate (p-nitrophenyl phosphate) at a concentration of 1 mg/ml in 1 M triethanolamine, pH 9.6. The color was allowed to develop for 7 min, and was stopped by addition of 3 M NaOH, 25 μl/well. The plate was then read on a Molecular Devices Vmax Kinetic Microplate Reader at 405 nm.

| Coating concentration rabbit × human IgG (mg/well) | Absorbance 405 nm (Mean of 4 wells) |
| --- | --- |
| 0 | 0.000 |
| $1 \times 10^{-5}$ | 0.122 |
| $3 \times 10^{-5}$ | 0.386 |
| $10 \times 10^{-5}$ | 1.097 |
| $30 \times 10^{-5}$ | 1.681 |
| $70 \times 10^{-5}$ | 1.882 |
| $100 \times 10^{-5}$ | 1.946 |

It is evident from the above results, that the subject methodology is highly efficient, simple, and produces functionalized surfaces which find a variety of uses. The clarity of the surface allows observation of the surface, where cells are being processed, transmission of light through the container, and the ability to monitor events in the container. In addition, the subject method provides for a very high density of molecules bound to the surface, where it is found that with antibodies, there is a high level of orientation of available binding sites. The smooth polystyrene surfaces are relatively free of cracks and crevices so that on a molecular scale, the proteins bound to the surface are available to binding of other molecules and cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for functionalizing a polystyrene surface, wherein said polystyrene is clear and at least substantially uncrosslinked to provide a high density of functional groups for covalently linking a moiety of interest to said surface, said method comprising:

contacting said polystyrene surface with an α-substituted N-(Y-methyl) acetamide in tetramethylenesulfone in the presence of a Lewis acid catalyst for sufficient time for displacement of Y by the benzene rings of said polystyrene to produce an acetamido substituted surface with retention of clarity, wherein said α-substituted group is a displaceable group by a nucleophilic substituent and Y is a group capable of electrophilic displacement by an aryl group in the presence of a Lewis acid catalyst.

2. A method according to claim 1, wherein said acidic catalyst is a protonic catalyst.

3. A method according to claim 2, wherein said acid catalyst is trifluoromethylsulfonic acid.

4. A method according to claim 1, wherein said α-substituent is a halogen or pseudohalogen.

5. A method according to claim 1, wherein said contacting is at a temperature in the range of about 0° to 40° C.

6. A method for functionalizing a polystyrene surface, wherein said polystyrene is clear and at least substantially uncrosslinked, to provide a high density of a moiety of interest covalently linked to said surface, wherein said moiety of interest comprises a group capable of nucleophilic substitution, said method comprising:

contacting said polystyrene surface with an α-substituted N-hydroxymethyl acetamide in tetramethylenesulfone in the presence of an acid catalyst for sufficient time for said N-hydroxymethyl acetamide to react with the benzene rings of said polystyrene to produce an acetamido substituted surface with retention of clarity, wherein said α-substituted group is a displaceable group by a nucleophilic substituent;

removing said tetramethylenesulfone solution; and contacting said acetamido substituted surface with said moiety of interest in a polar solvent, whereby said nucleophilic group becomes covalently bound to said surface at a high density.

7. A method according to claim 6, wherein said α-substituent is a halogen or pseudohalogen.

8. A method according to claim 6, wherein said moiety is a protein.

9. A method according to claim 8, wherein said protein is an antibody.

10. A polystyrene surface prepared according to the method of claim 1.

11. A polystyrene surface prepared according to claim 6.

12. A polystyrene surface prepared according to claim 9.

* * * * *